United States Patent

Sonoike et al.

Patent Number: 5,118,521
Date of Patent: Jun. 2, 1992

[54] METHOD OF PRODUCING BREAD CONTAINING OLIGOSACCHARIDE

[75] Inventors: Yoshiko Sonoike; Yoichi Kobayashi; Hisaaki Kato; Tatsuhiko Kan, all of Tokyo, Japan

[73] Assignee: Kabushiki Kaisha Yakult Honsha, Tokyo, Japan

[21] Appl. No.: 354,201

[22] Filed: May 19, 1989

[30] Foreign Application Priority Data

May 25, 1988 [JP] Japan ................. 63-125874

[51] Int. Cl.$^5$ ............ A21D 8/04; A23L 1/09
[52] U.S. Cl. .................. 426/549; 426/19; 426/20; 426/41; 426/43
[58] Field of Search .............. 426/20, 41–43, 426/549, 19

[56] References Cited

U.S. PATENT DOCUMENTS

| | | | |
|---|---|---|---|
| 3,466,176 | 9/1969 | Bundus et al. | 426/41 |
| 4,192,918 | 3/1980 | Steneman et al. | 426/41 |
| 4,332,895 | 6/1982 | Griffiths et al. | 426/41 |
| 4,944,952 | 7/1990 | Kobayashi et al. | 426/42 |

FOREIGN PATENT DOCUMENTS

| | | | |
|---|---|---|---|
| 1153614 | 9/1983 | Canada | 426/20 |
| 0197497 | 10/1986 | European Pat. Off. | |
| 0242459 | 10/1987 | European Pat. Off. | |
| 2080330 | 2/1982 | United Kingdom | |

OTHER PUBLICATIONS

Fennema, *Food Chemistry*, 1985, pp. 428–429; Marcel Dekker, Inc.

*Primary Examiner*—Donald E. Czaja
*Assistant Examiner*—Mary S. Mims
*Attorney, Agent, or Firm*—Oblon, Spivak, McClelland, Maier & Neustadt

[57] ABSTRACT

The present invention relates to a method of producing bread containing an oligosaccharide characterized by mixing an oligosaccharide expressed by the formula: Gal-(Gal)$_n$-Glc (wherein Gal denotes a galactose residue, Glc denotes a glucose residue and n denotes one of the integers from 1 to 4) in a raw material used for producing bread.

2 Claims, No Drawings

METHOD OF PRODUCING BREAD CONTAINING OLIGOSACCHARIDE

BACKGROUND OF THE INVENTION

The present invention relates to a method of producing bread (yeast bread) which contains an oligosaccharide functioning to promote the growth of Bifidobacterium bacteria and which has good taste and good preservability.

In recent years, various oligosaccharides, which are useful as substances for promoting growth of the Bifidobacterium bacteria that live in the human intestines and that are useful bacteria, have been employed significantly in the field of foods. In the area of bread, a method of producing bread containing oligosaccharides has been proposed in which fructooligosaccharide is mixed in the materials used for producing bread (refer to Japanese Patent Laid-Open Nos. 96942/1986 and 231992/1986, U. S. Pat. No. 4,693,898 and so forth). Fructooligosaccharide is an oligosaccharide in which 1 to 3 molecules of fructose connect with the fructose residue of sucrose (refer to Japanese Patent Laid-Open No. 96942/1986).

Since fructooligosaccharide is, however, a saccharide which is assimilated by normal bread yeasts and is thus decomposed in the process of fermentation, it does not remain in products even if it is mixed with the materials used for producing by normal methods. Thus, conventional methods of producing bread containing an oligosaccharide using fructooligosaccharide must employ a special bread yeast which does not decompose fructooligosaccharide (refer to Japanese Patent Laid-Open No. 96982/1986). Conventional methods, therefore, have a problem in that the process of production is inevitably changed to a large extent.

Accordingly, it is an object of the present invention to provide a method of producing bread containing an oligosaccharide which can be used with a normal bread yeast.

It is another object of the present invention to provide a method of producing bread containing an oligosaccharide and having good taste and preservability using a normal bread yeast.

SUMMARY OF THE INVENTION

The present invention provides a method of producing bread containing an oligosaccharide which is characterized by mixing an oligosaccharide expressed by the formula: Gal-(Gal)n-Glc (wherein Gal denotes a galactose residue, Glc denotes a glucose residue and n denotes one of the integers from 1 to 4) in the material used for producing bread.

DETAILED DESCRIPTION OF THE INVENTION

The present invention has been achieved on the basis of a finding obtained by the inventors that an oligosaccharide expressed by the formula: Gal-(Gal)n-Glc (wherein Gal denotes a galactose residue, Glc denotes a glucose residue and n denotes one of the integers from 1 to 4) is an oligosaccharide which cannot be consumed by any bread yeast. The present invention is characterized by employing galactrooligosaccharide as the oligosaccharide to be added. The production method of the present invention can therefore use a normal bread yeast that is generally used for producing bread (containing no oligosaccharide). As a matter of course, other special yeasts can be used in the production method of the present invention so far as they do not function to assimilate galactooligosaccharide.

Galactooligosaccharide used in the present invention can be produced by a method in which $\beta$-galactosidase derived from Asperoillus oryzae is reacted with lactose (Japanese Patent Publication No. 20266/1983), or yeast of Cryptococcus is used (Japanese Patent Laid-Open No. 251896/1985). The reaction product obtained by reaction of lactose with $\beta$-galactosidase, however, comprises transfer disaccharides, glucose, galactose and unreacted lactose as well as galactooligosaccharide. The reaction between the reaction product and $\beta$-galactosidase derived from another bacteria source enables a reduction in the amount of the unreacted lactose. It is therefore possible to obtain galactooligosaccharide in a reaction product containing a high ratio of galactooligosaccharide produced by the above-described method and then purifying the product by any desired method, as occasion demands. Even if an unpurified sugar mixture in which disaccharides and monosaccharides coexist is mixed in a material used for producing bread, since the monosaccharides are employed as sugar sources for fermentation and the galactooligosaccharide and other nonfermentable saccharides remain in the product, the sugar mixture can be used as it normally is for producing bread. The method which uses the unpurified sugar mixture allows the utilization of oligosaccharides at low cost and with a reduction in the amount of the fermentation sugar sources added, thus exhibiting an economical advantage as well.

When the above-described galactooligosaccharide or sugar mixture containing it is added to a material used for producing bread, the amount of galactooligosaccharide mixed is not particularly limited. Since galactooligosaccharide has a low degree of sweetness and neither taste nor odor, the addition of a large amount (for example, about 10% by weight) of galactooligosaccharide has no adverse effect on the taste of the bread produced. When galactooligosaccharide accompanied with monosaccharides is used, however, the fermentaton and strong sweetness of the monosaccharides affect the fermentation process in the production of bread and the quality of products. In such a case, therefore, the amount of the sugar mixture added is limited so that the amount of the monosaccharides mixed is about 5 to 20 g relative to 500 g of a material used for producing bread, or a sugar mixture is used in combination with galactooligosaccharide.

Since fermentable saccharides are generally necessary as nutrient sources for yeasts and significantly affect the physical properties of baked products such as color tones and rising and taste and odor, sufficient amounts of fermentable saccharides can be mixed in materials for bread. When galactooligosaccharide accompanied with no fermentable monosaccharide is used in the production method of the present invention, or when the amount of the monosaccharides accompanying galactooligosaccharide is insufficient as nutrient sources or insufficient to improve the flavor of the product, sucrose, glucose, inverted sugar or the like is appropriately added. Salt, oil or fat, dairy products, additives and so forth can be used in accordance with normal methods, as occasion demands.

Preparation of a dough, fermentation, shaping, roasting, baking and so on can be performed by normal methods using a raw material for producing bread which contains galactooligosaccharide or a sugar mixture containing it.

EXAMPLE

The present invention will be described below with reference to the examples.

EXAMPLE 1

After dissolving 4 kg of food-grade lactose in 2.4 l of hot water, 80000 units of β-galactosidase derived from Aspergillus oryzae were added to the thus-formed solution, followed by reaction at 67° C. for 2 hours. The reaction product was then heated at 95° C. for 10 minutes so that the enzyme was deactivated. After the reaction solution had been diluted to 50% of a solid concentration, 5000 units of β-galactosidase prepared from Streptococcus thermophilus were added to the diluted solution, which was then reacted at 45° C. for 40 hours. The reaction solution was then heated at 90° C. for 10 minutes so that the enzyme was deactivated, and was then filtered using a carbon powder and Celite, which were added thereto. The filtrate was then desalted by using an ion-exchange resin.

A 58 g concentrated solution of the thus-obtained sugar solution (solid concentration, 75 w/w %; sugar composition: galactooligosaccharide 37%, disaccharides 26%, monosaccharides 37%) was dissolved in 170 g of water. The thus-formed solution was then kneaded with 280 g of wheat flour, 5 g of salt, 6 g of skim milk powder and 11 g of butter, and 3 g of bread yeast powder were then added to the thus-formed mixture and kneaded therewith. After the thus-formed mixture was fermented for 2 hours, it was baked in an oven.

The thus-obtained bread was soft and full and had a glossy surface, a soft interior and a uniform and fine texture.

Comparison with the bread produced as a control by the same method as that described above with the exception that sucrose was used in place of the sugar solution containing galactooligosaccharide showed that the two types of bread had the same weight and volume.

Table 1 shows the results obtained by measurements of the sugar contents by using high speed liquid chromatography in the course of production of the bread and at the final stage thereof. When a bread dough is baked, the contents of oligosaccharides and disaccharides are increased in some cases owing to the production of such saccharides from the glucide in the wheat flour during the baking process. The analytical values shown in Table 1 were therefore obtained by correcting as a blank the analytical value of the bread which was baked using no oligosaccharidess.

TABLE 1

| | Sugar Content per 1.232 lb of Bread (g) | | | |
|---|---|---|---|---|
| | Oligo saccharide | Di- saccharide | Glucose | Galactose |
| Before fermentation | 14.7 | 24.3 | 10.1 | 4.2 |
| After fermentation | 14.5 | 22.0 | 2.9 | 2.7 |
| After baking | 14.9 | 23.8 | 0.3 | 3.0 |

EFFECT OF THE INVENTION

As described above, since the method of producing bread containing an oligosaccharide of the present invention uses galactrooligosaccharide which is not consumed by any bread yeast, a normal bread yeast can be used, and thus there is no need for use of a special yeast which does not ferment oligosaccharides. Although bread is presently produced by innumerable large and small scale bread manufactures, and many kinds of bread are produced, the proper use of bread yeasts is not generally conducted. When bread containing an oligosaccharide is produced, therefore, the preparation of a special yeast used for this purpose alone causes complications in the control of materials and the fermentation process and increases in the production cost. Yeasts of the type generally used in bread manufacturing at present are excellent strains carefully selected in the course of a long history of bread production from the viewpoint of bread taste and workability of the production process. Considering the above, it is apparent that the production method of the present invention which enables the use of these bread yeasts generally used can be very useful.

Galactooligosaccharide which is produced by β-galactosyl transfer reaction of lactose can be obtained in the form of a mixture at a low cost containing monosaccharides such as glucose, galactose and so on which are secondary products. Since such monosaccharides can be employed as nutrient sources for yeasts and have an excellent quality of sweetness, they can be used in the same manner as they normally are in the production method of the present invention. It is thus possible to reduce the necessary amount of fermentable sugar mixed such as sucrose by an amount equivalent to the amount of the monosaccharides added. In other words, the method using a mixture containing monosaccharides is a production method which has excellent economic advantages. Since fermentation of galactose or monosaccharides proceeds at a speed that is lower than that of glucose, galactose has a tendency to remain to some extent in products but has advantages in that it functions to improve the color of the baked bread and impart a particular fragrance thereto.

In addition, the bread produced by the method of the present invention is very moistureproof and resists deterioration. That is, although freezing is superior to refrigeration as a method of preservation, normal bread becomes dry after being thawed out. However, such deterioration does not easily occur in the bread produced by the method of the present invention.

What is claimed is:

1. A method of producing a raw material used for the production of bread, comprising: mixing an oligosaccharide of the formula:

Gal-(Gal)$_n$-Glc wherein Gal denotes a galactose residue, Glc denotes a glucose residue and n is a integer from 1 to 4, into the raw materials used for the production of bread, wherein said oligosaccharide is incorporated into said raw material in an amount of at least about 2.6% by weight.

2. A method for the preparation of a bread material useful for the production of bread, comprising:

mixing a sugar mixture containing an oligosaccharide of the formula:

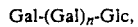

Gal-(Gal)$_n$-Glc, wherein Gal denotes a galactose residue, Glc denotes a glucose residue and n is an integer from 1–4, transfer disaccharides, glucose and galactose into a raw material useful for the production of bread, said sugar mixture being obtained by reacting lactose with β-galactosidase, wherein said oligosaccharide is incorporated into said new material in an amount of at least about 2.6% by weight.

* * * * *